United States Patent [19]

Sun

[11] Patent Number: 4,915,108
[45] Date of Patent: Apr. 10, 1990

[54] HOT AND COLD COMPRESS DEVICE

[76] Inventor: Shin-Ching Sun, 3F., No. 32, 132nd Lane, Hu-Lin St., Taipei, Taiwan

[21] Appl. No.: 202,251

[22] Filed: Jun. 6, 1988

[51] Int. Cl.$^4$ .............................................. A61F 7/00
[52] U.S. Cl. ................................. 128/402; 128/399; 219/211
[58] Field of Search ............... 128/399, 400, 402, 379; 165/46; 62/259.3, 3; 219/265, 211

[56] References Cited

U.S. PATENT DOCUMENTS

| | | | |
|---|---|---|---|
| 1,327,207 | 1/1920 | Lidberg | 128/400 |
| 2,938,356 | 5/1980 | McMahon | 128/399 |
| 3,080,723 | 3/1963 | Price | 128/399 |
| 4,523,594 | 6/1985 | Kuznetz | 128/402 |
| 4,585,002 | 4/1986 | Kissin | 128/399 |

Primary Examiner—Edward M. Coven
Assistant Examiner—M. Graham
Attorney, Agent, or Firm—Browdy and Neimark

[57] ABSTRACT

A hot and cold compress device comprises a heat transmitted element of which one plate grows hot or the other plate grows cold while the current is conducting, a pair of heat conduct elements which can conduct the aforesaid heat transmitted element to grow hot or cold, an adiabatic tie which sleeves the heat transmitted element and the heat conduct elements, two radiating films which are installed symmetrically to coat the two surfaces of the adiabatic tie, two thermometers which are united on the end of the radiating films, a control box which supplies the power of the heat transmitted element and sets the temperature, and a pair of ties which are connected to the two ends of the adiabatic tie. The feature of the present invention is that the device grows cold at one side of the radiating films, while conducting, to reduce the patient's fever. On the other hand, if the polarity of the power supply is changed and reversed, the other side of the radiating films grows hot to provide the patient a hot compress.

3 Claims, 2 Drawing Sheets 4,915,108

HOT AND COLD COMPRESS DEVICE

FIELD OF THE INVENTION

1. Background of the Invention

The present invention relates to a kind of hot and cold compress device for use by humans. Particularly, it relates to an invention that is a kind of tie device to provide the hot or cold compress for the patient. When the power is supplied, one plate of the tie will grow cold to provide a cold compress on the patient's head and to reduce his fever. When the polarity of the power supply is reversed, the other one plate of the tie can provide the hot compress on the needed position of the patient.

2. Prior Art

Generally, doctors always give a febrifuge or a shot to reduce the patient's fever. They also use the ice bag to provide a cold compress on the patients head in order to avoid the fever damaging the patient's brain organization. That method can achieve really some suitable effect; however, when the ice bag contacts with the hot air, the vapor of the air will condense into the drops on the surface of the ice bag. It makes the outer surface of the ice bag moisten and produce moisture. When the ice blocks are gradually melted into water and the temperature ascends, it become necessary to spill the water and to fill the bag with some ice blocks again. Therefore, using an ice bag is really troublesome. Besides, some patients are asked to take a hot compress with a water bag during their healing process. The object of using a hot compress is to increase the circulation of the blood and the speed of the patient's recovery. It really has some effect. The temperature of the water, however, is not continuely maintained. It is necessary to change the hot water many times in order to maintain the suitable temperature. Therefore, using a water bag is also troublesome and cannot avoid the problems of vapor and moisture.

SUMMARY OF THE INVENTION

According to one aspect of the invention, a hot and cold compress device comprises a heat transmitted element of which one plate grows hot or the other plate grows cold while the current is conducting, a pair of heat change elements which can conduce the aforesaid heat transmitted element to grow hot or cold, an adiabatic tie which sleeves the heat transmitted element and the heat conduct elements, two radiating films which are installed symmetrically to coat the two surfaces of the adiabatic tie, two thermometers which are united on the end of the radiating films, a control box which supplies the power of the heat transmitted element and sets the temperature, and a pair of ties which are connected the two ends of the said adiabatic tie. One side of the radiating films grows cold by the power supplying of the control box to provide a cold compress for the patient's head. On the other hand, if the polarity of the power supply is changed to reverse, the other side of the radiating films will grow hot to provide the hot compress for the patient. The present invention can maintain constant temperatures and its use is convenient.

SPECIFIC DESCRIPTION

Figure 1:
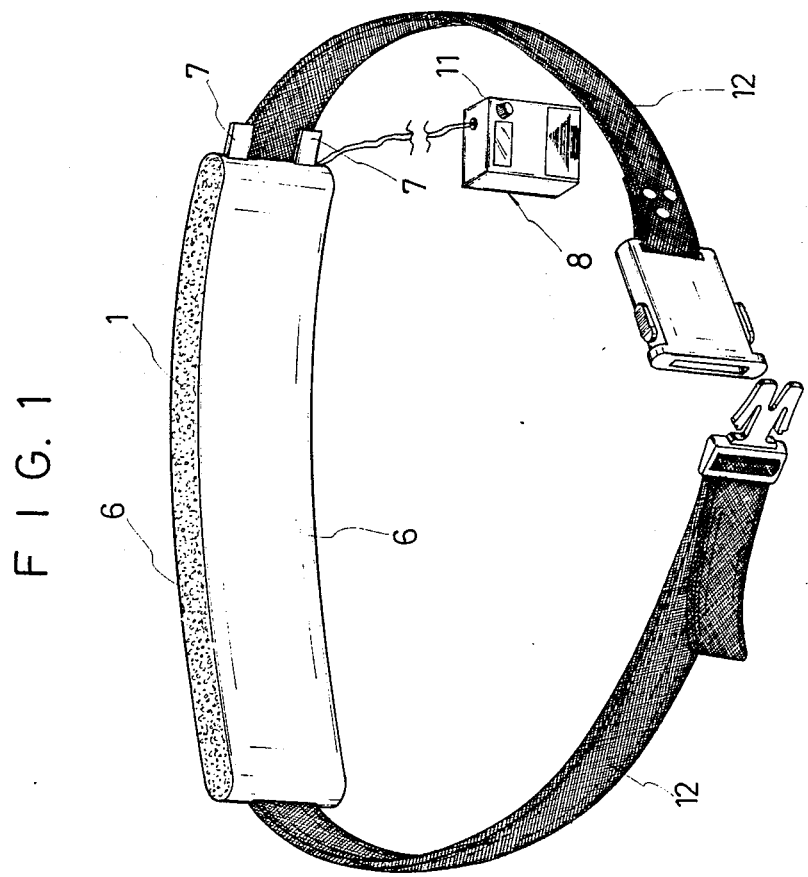
FIG. 1 is a diagram of the appearance in accordance to present invention.
Figure 2:
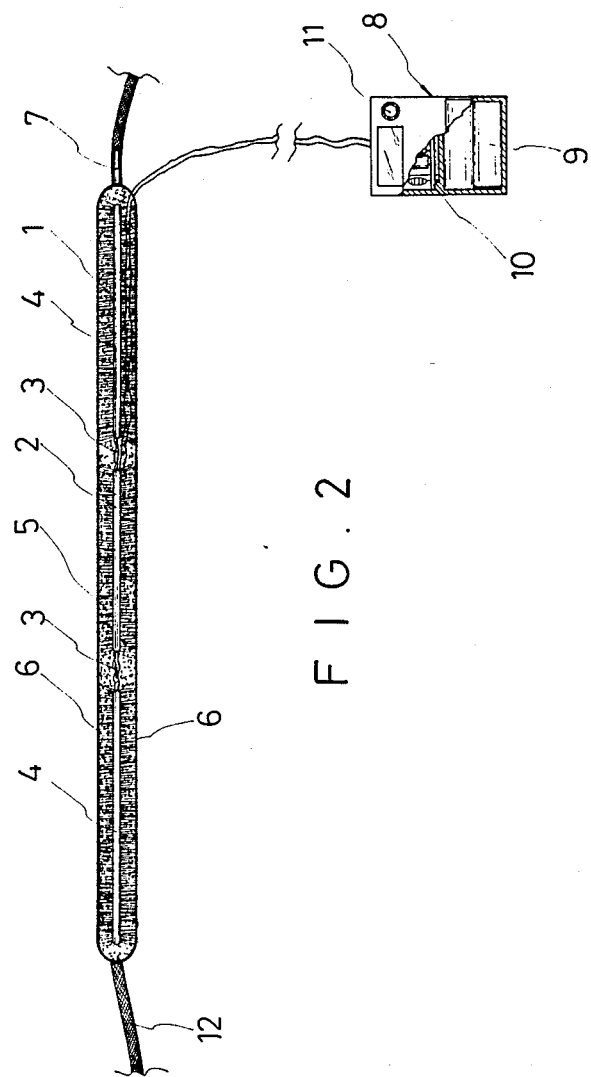
FIG. 2 is a sectional view showing the inner structure of FIG. 1.

As showing in FIGS. 1 and 2, the present invention uses a suitable wide, thick and long adiabatic tie 1 to be the body. The adiabatic tie 1 is made of a kind of porous material and forms a sleeve surrounding a heat transmitted element 2. At the two sides of the heat transmitted element 2, the heat conducting elements 4 are connected to the heat transmitted element 2 by the wires 3. On the surface of the heat conducting elements 4 and the heat transmitted element 2, a number of radiating ribs 5 are connected which pass through the adiabatic tie 1 to the surface and become the radiating films 6. The radiating films are made of a mixture of aluminized lead and silicone jelly. When the heat transmitted element 2 is electrified, one side of the radiating films 6 will grow cold. If the polarity of the current is changed and revised, the other side of the radiating films 6 will grow hot. Liquid crystal display thermometer 7 are installed on one side of the adiabatic tie 1, as shown in FIG. 1, which can show exactly the hot or cold temperature of the two radiating films 6. The power wires of the heat transmitted element 2 pass through the end of the adiabatic tie 1 to connect to the control box 8. In the said control box 8 batteries 9 are provided and a circuit board 10 is installed, and a temperature adjusting device 11 is also installed to adjust the set temperature. At the two ends of the adiabatic tie 1 ties 12 are connected respectively, to unite the compress to the head or the other place of patient.

The present invention uses the batteries 9 of the control box 8. When the present invention is electrified, it is only required to adjust and set the suitable temperature, then tie the present invention on the head or the other required position of the patient. The device achieves the effect of a hot or cold compress depending on the polarity of the current.

I claim:

1. A hot and cold compress device, comprising:
   a wide, thick and elongated adiabatic tie formed of a porous material for placement adjacent a portion of a patient's body;
   a heat transmitted element disposed within said adiabatic tie such that said adiabatic tie forms a sleeve surrounding said heat transmitted element;
   two heat conducting elements disposed within said adiabatic tie and connected, respectively, to an end of said heat transmitted element;
   a plurality of radiating ribs connected to surface portions of said heat conducting elements and said heat transmitted element passing through said adiabatic tie;
   radiating films disposed on outside surfaces of said adiabatic tie connected to said plurality of radiating ribs, said radiating films being made of a mixture of aluminized lead and silicone jelly;
   at least one thermometer connected to an end of said radiating films for showing the temperature of said radiating films;
   a control box for controlling said compress device, said control box comprising at least one battery and a temperature adjusting set device for controlling the temperature of said radiating films;
   power wires connected between said heat transmitted element and said control box, and wherein said control box controls the temperature of said radiating films to cause said films to grow hot or cold to provide, respectively, a hot or cold compress for the patient.

2. The hot and cold compress device according to claim 1, further comprising
two ties having first ends connected to opposite ends of said adiabatic tie, respectively for removably holding said adiabatic tie adjacent the portion of the patient's body.

3. The hot and cold compress device according to claim 1, wherein said at least one thermometer comprises two liquid crystal display thermometers.

* * * * *